US008591403B2

(12) United States Patent
Yoshida et al.

(10) Patent No.: US 8,591,403 B2
(45) Date of Patent: Nov. 26, 2013

(54) WIRELESS POWER SUPPLY SYSTEM, CAPSULATED ENDOSCOPE, AND CAPSULATED ENDOSCOPIC SYSTEM

(75) Inventors: Naoki Yoshida, Nagano (JP); Youhei Sakai, Ina (JP)

(73) Assignee: Olympus Corporation, Tokyo (JP)

( * ) Notice: Subject to any disclaimer, the term of this patent is extended or adjusted under 35 U.S.C. 154(b) by 1041 days.

(21) Appl. No.: 12/018,603

(22) Filed: Jan. 23, 2008

(65) Prior Publication Data
US 2008/0177143 A1 Jul. 24, 2008

(30) Foreign Application Priority Data

Jan. 24, 2007 (JP) ................................ 2007-014171

(51) Int. Cl.
*A61B 1/00* (2006.01)
*A61B 1/04* (2006.01)
*A61B 1/06* (2006.01)
(52) U.S. Cl.
USPC ........................... 600/130; 600/109; 600/160
(58) Field of Classification Search
USPC ............ 600/40, 109, 130, 160, 407; 307/104; 343/895
See application file for complete search history.

(56) References Cited

U.S. PATENT DOCUMENTS

| | | | | |
|---|---|---|---|---|
| 3,742,341 A * | 6/1973 | Clowes et al. | ................. | 324/329 |
| 5,741,316 A * | 4/1998 | Chen et al. | ....................... | 607/61 |
| 6,201,387 B1 * | 3/2001 | Govari | ..................... | 324/207.17 |
| 6,273,904 B1 * | 8/2001 | Chen et al. | ...................... | 607/88 |
| 7,354,398 B2 * | 4/2008 | Kanazawa | ..................... | 600/109 |
| 7,604,591 B2 * | 10/2009 | Uchiyama et al. | ............. | 600/130 |
| 8,378,523 B2 * | 2/2013 | Cook et al. | ..................... | 307/104 |
| 2002/0103417 A1 * | 8/2002 | Gazdzinski | ................... | 600/109 |
| 2002/0165592 A1 | 11/2002 | Glukhovsky et al. | | |
| 2003/0164805 A1 * | 9/2003 | Strickland | ..................... | 343/895 |
| 2005/0216231 A1 | 9/2005 | Aoki et al. | | |
| 2005/0228259 A1 * | 10/2005 | Glukhovsky et al. | ......... | 600/407 |
| 2007/0164900 A1 * | 7/2007 | Schneider et al. | ........ | 342/357.12 |
| 2007/0290814 A1 * | 12/2007 | Yoshida | ..................... | 340/10.34 |
| 2008/0070499 A1 * | 3/2008 | Wilhelm et al. | ............. | 455/41.1 |
| 2009/0273242 A1 * | 11/2009 | Cook | ............................. | 307/104 |

(Continued)

FOREIGN PATENT DOCUMENTS

JP 57-131042 U 8/1982
JP 07-169627 A 7/1995

(Continued)

OTHER PUBLICATIONS

English language abstract only of WO 02/080753 A2 dated Oct. 17, 2002.

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

In a wireless power supply system including a power feeding system equipped with a transmission antenna for wirelessly transmitting an electric power from a power source, and a receiver antenna formed by winding a receiver coil around an outer periphery of a substantially bar-like core member for receiving the transmitted electric power, the length of the core member of the receiver antenna is more than 10 times longer than the diameter of the core member.

2 Claims, 7 Drawing Sheets

(56) References Cited

U.S. PATENT DOCUMENTS

| | | | |
|---|---|---|---|
| 2009/0294065 A1* | 12/2009 | Lai et al. | 156/345.47 |
| 2010/0164823 A1* | 7/2010 | Kubo et al. | 343/788 |
| 2010/0194334 A1* | 8/2010 | Kirby et al. | 320/108 |
| 2010/0253089 A1* | 10/2010 | Huang et al. | 290/1 R |
| 2010/0264747 A1* | 10/2010 | Hall et al. | 307/104 |
| 2011/0089895 A1* | 4/2011 | Karalis et al. | 320/108 |
| 2011/0095617 A1* | 4/2011 | Cook et al. | 307/104 |

FOREIGN PATENT DOCUMENTS

| | | |
|---|---|---|
| JP | 2001-224551 | 8/2001 |
| JP | 2003-088535 A | 3/2003 |
| JP | 2003-264423 A | 9/2003 |
| JP | 2004-528890 A | 9/2004 |
| JP | 2005-062161 A | 3/2005 |
| JP | 2005-245963 A | 9/2005 |
| JP | 2006-118925 A | 5/2006 |
| JP | 2006-149687 | 6/2006 |
| JP | 2006306184 A | 11/2006 |
| JP | 2007-082816 | 4/2007 |
| WO | WO 2007/124970 A1 | 11/2007 |

OTHER PUBLICATIONS

Japanese Official Action dated May 7, 2013 received in related application JP 2007-014171.

* cited by examiner

| ASPECT RATIO | CORE DIAMETER [mm] | CORE LENGTH [mm] | WINDING NUMBER OF COIL [NUMBER] | COIL WIRE RADIUS [mm] | CORE MATERIAL | NORMALIZED RECEIVING POWER [TIMES] |
|---|---|---|---|---|---|---|
| 1 | 1.0 | 1 | 50 | 0.2 | FERRITE PRODUCED BY COMPANY A | 1 |
| 3 | | 3 | | | | 9.99 |
| 5 | | 5 | | | | 35.8 |
| 10 | | 10 | | | | 247 |
| 12 | | 12 | | | | 420 |
| 15 | | 15 | | | | 830 |

US 8,591,403 B2

WIRELESS POWER SUPPLY SYSTEM, CAPSULATED ENDOSCOPE, AND CAPSULATED ENDOSCOPIC SYSTEM

This application claims benefit of Japanese Application No. 2007-014171 filed on Jan. 24, 2007 the contents of which are incorporated by this reference.

BACKGROUND OF THE INVENTION

1. Field of the Invention

The present invention relates to a wireless power supply system equipped with a receiver antenna for converting an external magnetic field into an electric power, a capsulated endoscope equipped with the wireless power supply system, and a capsulated endoscopic system.

2. Description of the Related Art

Generally, a miniature endoscope which contains observation means including an image pickup optical system, illumination means including an illumination optical system, communication means, a power source, and power receiving means inside a capsular case, that is, a capsulated endoscope has been developed as a medical system for inspecting inside the body cavity or the like. The capsulated endoscope forms a capsulated endoscopic system together with a communication unit for performing a wireless communication, memory means for storing a received signal, and a wireless power supply system for wirelessly supplying the electric energy externally using the AC magnetic field. The aforementioned capsulated endoscopic system is disclosed in Japanese Unexamined Patent Application Publication No. 2001-224551, for example.

The generally employed capsulated endoscopic system contains a receiver antenna coiled to surround the inner wall of the capsulated endoscope.

The electric energy fed from the transmission antenna of the wireless power supply system is received by the receiver antenna of the capsulated endoscope, and further fed to the capsulated endoscope being used in the body cavity from the wireless power supply system disposed outside the body.

SUMMARY OF THE INVENTION

In the first aspect of the present invention, a wireless power supply system includes a power feeding system equipped with a transmission antenna for wirelessly transmitting an electric power from a power source, and a receiver antenna formed by winding a receiver coil around an outer periphery of a substantially bar-like core member for receiving the transmitted electric power. A length of the core member of the receiver antenna is more than 10 times longer than a diameter of the core member.

In the second aspect of the present invention, a capsulated endoscope includes a receiver antenna formed by winding a receiver coil around an outer periphery of a substantially bar-like core member for wirelessly receiving an electric power. A length of the core member of the receiver antenna is more than 10 times longer than a diameter of the core member.

In the third aspect of the present invention, a capsulated endoscopic system includes a power feeding system equipped with a transmission antenna for wirelessly transmitting an electric power from a power source, and a capsulated endoscope which contains a receiver antenna formed by winding a receiver coil around an outer periphery of a substantially bar-like core member for receiving the transmitted electric power. A length of the core member of the receiver antenna is more than 10 times longer than a diameter of the core member.

The above and other objects, features and advantages of the invention will become more clearly understood from the following description referring to the accompanying drawings.

DETAILED DESCRIPTION OF THE PREFERRED EMBODIMENTS

Figure 1:
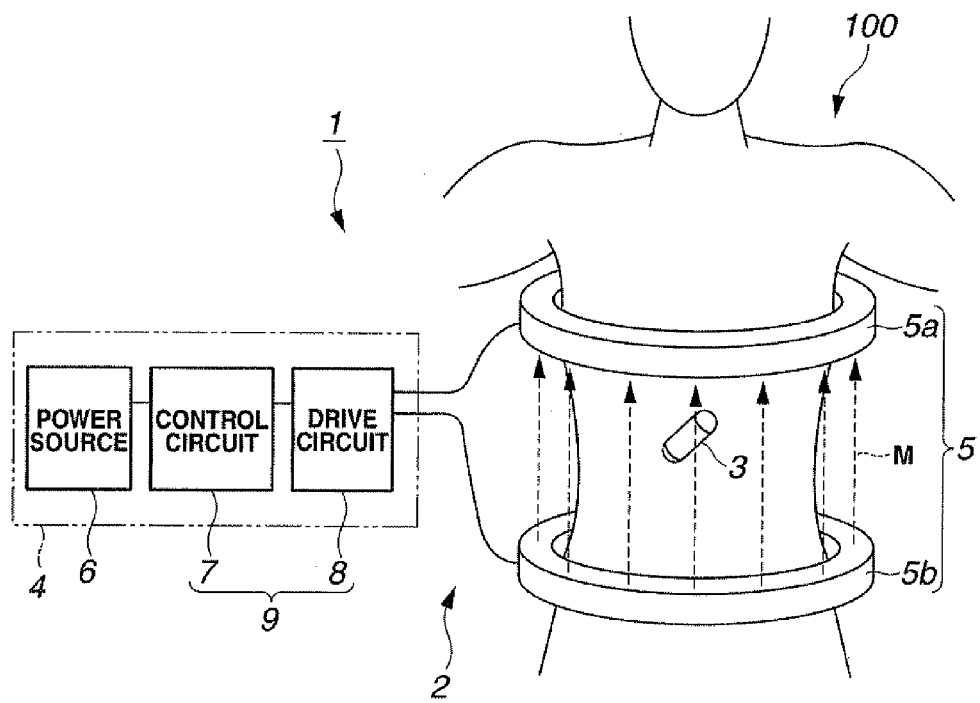
FIG. 1 is a view showing a structure of a capsulated endoscopic system according to a first embodiment, and a state where a capsulated endoscope has been taken into a body cavity of a subject body.

Embodiments of the present invention will be described referring to the drawings. The wireless power supply system according to the embodiments as described below will be described with respect to the capsulated endoscope.

First Embodiment

Figure 2:
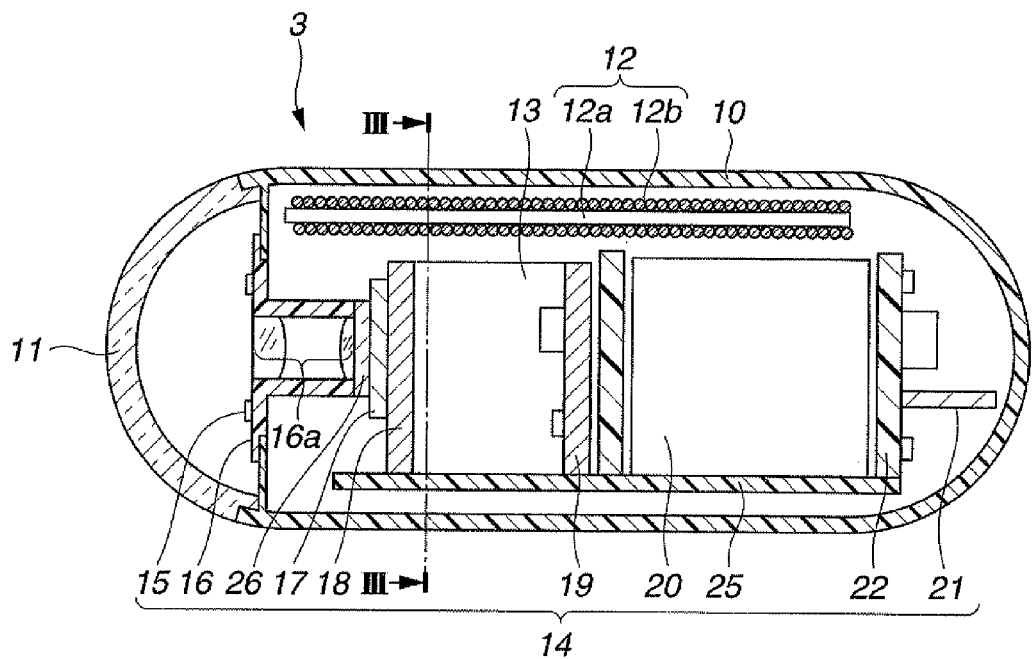
FIG. 2 is a cross-sectional view of the capsulated endoscope equipped with a receiver antenna.
Figure 3:
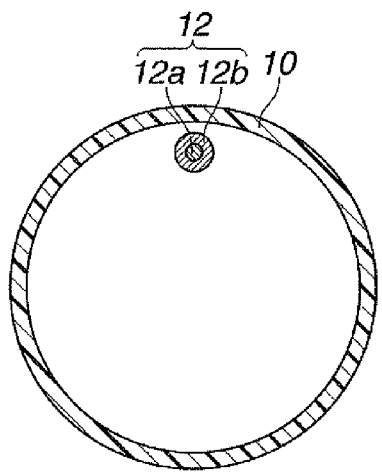
FIG. 3 is a cross-sectional view taken along line III-III shown in FIG. 2 as a front view of the capsulated endoscope in a cylindrical direction.
Figure 4:
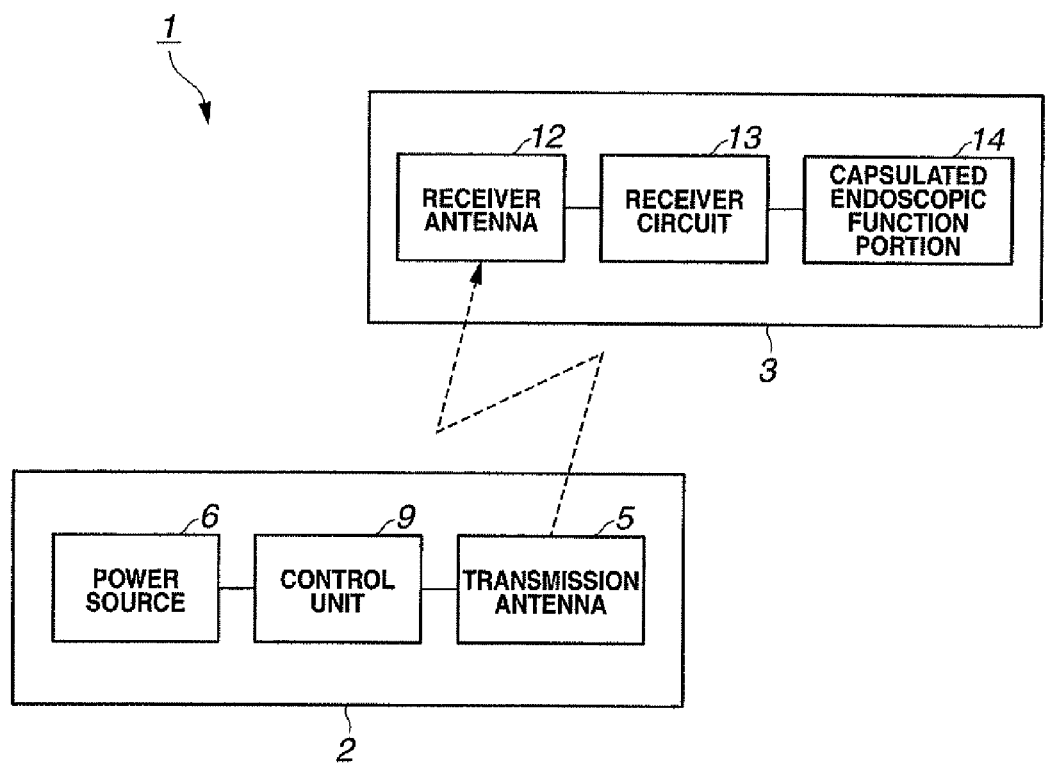
FIG. 4 is a block diagram showing the capsulated endoscope and the power feeding system.
Figure 5:
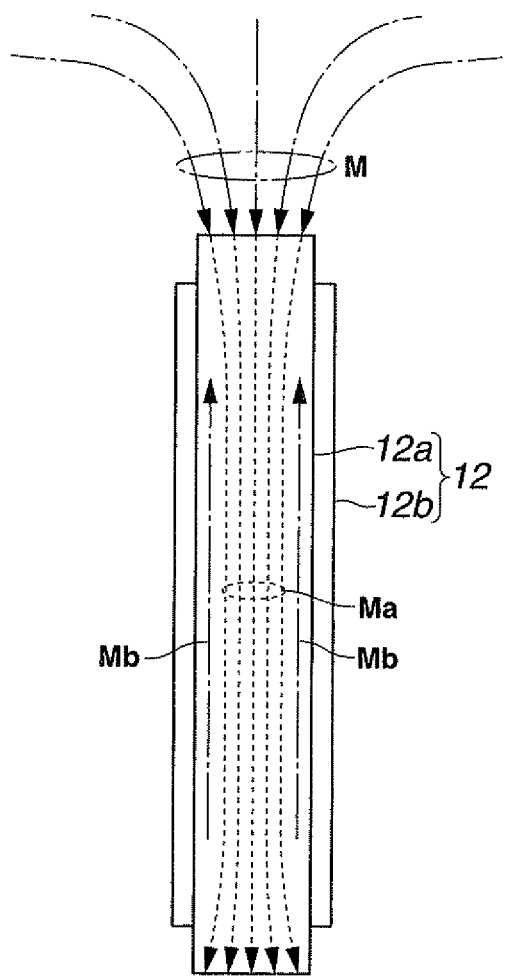
FIG. 5 is an explanatory view of the magnetic fluxes passing inside the core of the receiver antenna.
Figures 6, 7:
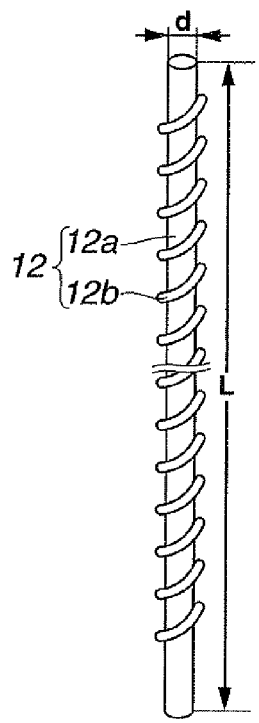
FIG. 6 is a view showing the structure of the receiver antenna.
FIG. 7 is a table showing the relationship between the electric power to be received and the aspect ratio under a constant magnetic field while changing the aspect ratio of the core.
Figure 8:
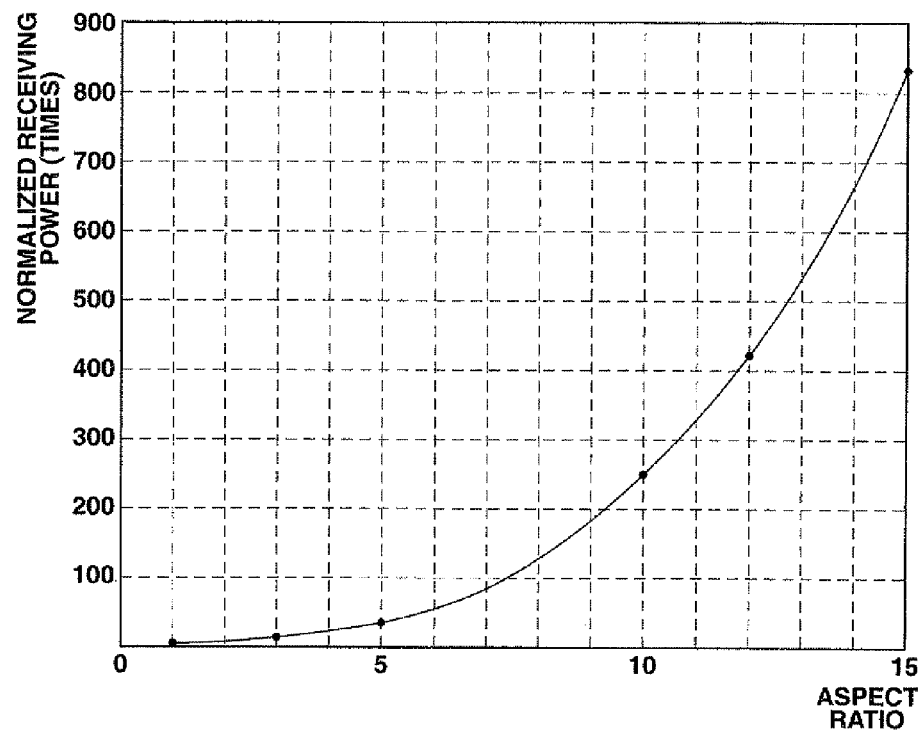
FIG. 8 is a graph showing the relationship between the aspect ratio and the electric power to be received, which reflects the results of the table in FIG. 7.
Figure 9:
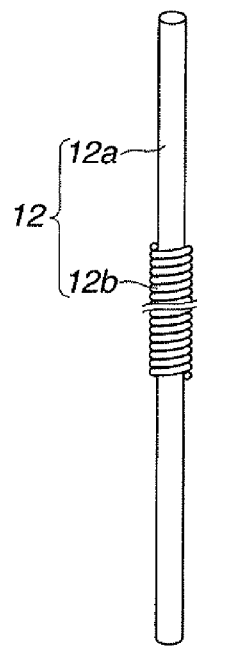
FIG. 9 is a view showing the structure of the receiver antenna as a modified example.

A first embodiment of the present invention will be described referring to FIGS. 1 to 9. FIG. 1 is a view showing a structure of a capsulated endoscopic system, and a state where a capsulated endoscope has been taken into a body cavity of a subject body. FIG. 2 is a cross-sectional view of the capsulated endoscope equipped with a receiver antenna. FIG. 3 is a cross-sectional view taken along line III-III shown in FIG. 2 as a front view of the capsulated endoscope in a cylindrical direction. FIG. 4 is a block diagram showing the capsulated endoscope and the power feeding system. FIG. 5 is an explanatory view of the magnetic fluxes passing inside the core of the receiver antenna. FIG. 6 is a view showing the structure of the receiver antenna. FIG. 7 is a table showing the relationship between the electric power to be received and the aspect ratio under a constant magnetic field while changing the aspect ratio of the core. FIG. 8 is a graph showing the relationship between the aspect ratio and the electric power to be received, which reflects the results of the table in FIG. 7. FIG. 9 is a view showing the structure of the receiver antenna as a modified example.

Referring to FIG. 1, a capsulated endoscopic system 1 according to the embodiment includes a power feeding system 2 and a capsulated endoscope 3 which form the wireless power supply system.

The power feeding system 2 formed of a main body 4 and a transmission antenna 5 for wirelessly transmitting the electric energy is placed outside the subject body. The main body 4 contains a power source 6, a control circuit 7 and a drive circuit 8 which are electrically coupled with one another. In the embodiment, the control circuit 7 and the drive circuit 8 form a control unit 9.

The control unit 9 controls the output of the power source 6 for controlling the output of the transmission antenna 5 such that the AC magnetic field generated by the transmission antenna 5, that is, the feeding power is adjusted.

The transmission antenna 5 includes two ring-like antenna portions 5a and 5b as Helmholtz type coils, which are electrically coupled with the drive circuit 8 of the main body 4. Those antenna portions 5a and 5b are put on a torso of a subject 100 so as to be apart from each other by a predetermined interval.

The thus structured power feeding system 2 applies the alternate current generated by the power source 6 and the control circuit 7 to the transmission antenna 5. Upon reception of the alternate current, the transmission antenna 5 generates the AC magnetic field corresponding to the applied alternate current to generate a magnetic flux M directed from the antenna portion 5b to the antenna portion 5a in the body of the subject. Besides the Helmholtz coil, an arbitrary coil, for example, the solenoid coil or other type of coil may be employed as the transmission antenna 5.

A capsulated endoscope 3 with a capsule tablet-like outer appearance as shown in FIG. 1 is swallowed by the subject to be taken into the body cavity.

Referring to FIG. 2, the capsulated endoscope 3 are sealed by an outer case 10 having both ends formed as substantially dome-like capsule type, and a transparent cover 11 set at one end of the outer case 10. A receiver antenna 12, a receiver circuit 13, and a capsulated endoscope function portion 14 are placed inside the outer case 10.

The receiver antenna 12 includes a cylindrical thin and long core 12a formed of a ferromagnetic material, and a receiver coil 12b wound around the outer periphery of the core 12a. The receiver coil 12b is wound around the core 12a uniformly. The shape of the core 12a is not limited to the substantially bar-like cylinder, but may be formed to have the multiangular cross section such as the rectangular shape and the octagonal shape so long as it has a pillar shape. The core 12a may also be formed as an annular shape.

The core 12a is formed of a high magnetic permeability magnetic material, for example, a metal alloy material, a ferrite material, and an amorphous magnetic material. As shown in FIG. 3, the core 12a is placed adjacent to the inner periphery of the outer case 10 to have a long bar-like shape.

The receiver circuit 13 includes a rectifying circuit such as a diode bridge for rectifying the alternate current and a smoothing circuit such as a capacitor functioning as an energy storage element and a ripple attenuation element in the capsulated endoscope for conversion into the electric power received by the receiver antenna 12. Explanation or illustration of those generally employed circuits will be omitted.

Illustration of a resonant capacitor connected to the receiver antenna 12 so as to be resonated with the frequency of the externally applied AC magnetic field will also be omitted.

The capsulated endoscope function portion 14 includes a light emitting diode (LED) 15 for illumination as illumination means, and a lens frame 16 provided with a lens group 16a as an image pickup optical system to form the image of the subject on the light receiving surface of the image pickup device 26 to be described later. The capsulated endoscope function portion 14 further includes an image pickup device 26 formed of an image sensor such as CMOS and CCD as a photoelectric conversion element for performing the photoelectric process for converting the received optical image of the subject into the electric signal.

The capsulated endoscope function portion 14 further includes an image pickup device drive unit 17 for performing the drive control of the above-mentioned image pickup device 26, a signal processing unit 18, a receiver circuit 19 connected to the receiver antenna 12, an emergency battery 20, and a modulation transmission amplifier 22 for modulating and amplifying the predetermined signal upon reception of the electric signal (image signal) outputted from the image pickup device 26 including a transmission antenna 21 for transmitting the shot image to the outside. The aforementioned elements in the predetermined arrangement are placed on a rigid substrate or an FPC electric substrate 25.

The image pickup device 26 functions in picking up the site irradiated by the LED 15. The image pickup device 26, the image pickup optical system including the lens group 16a, and the image pickup device drive unit 17 and the like form the image pickup means. The image pickup means functions in obtaining the electric image signal for displaying the state inside the body cavity on the observation screen of the image display unit as the observation image.

The modulation transmission amplifier 22, the transmission antenna 21 and the like form the transmission means for transmitting the image signal obtained by the image pickup means to the receiver means of the power feeding system 2 disposed outside the body. The transmission means performs a predetermined signal processing upon reception of the image signal which has been processed by the signal processing unit 18, and then transmits the processed image signal to the outside.

In the above-structured capsulated endoscopic system 1 of the embodiment the image signal obtained through the image pickup operation of the image pickup means of the capsulated endoscope 3 is processed to data by the signal processing unit 18, and then transmitted to the power feeding system 2 via the transmission means (modulation transmission amplifier 22 and the transmission antenna 21) such that the power feeding system 2 receives the image data signal. The power feeding system 2 then receives the image data signal.

The image data signal received by the power feeding system 2 is subjected to the predetermined signal processing in the inner circuit, and transmitted to the image display unit (not shown). The image data signal is further subjected to the predetermined signal processing to the image signal in the mode optimal for the display, and then displayed on the display portion of the image display unit as the image shot by the image pickup means.

Referring to FIG. 4, the power feeding system 2 transmits the electric energy from the transmission antenna 5 based on the wireless power feeding mode under the control of the power source 6 by the control unit 9. The receiver antenna 12 of the capsulated endoscope 3 receives the electric energy from the transmission antenna 5 so as to be transmitted to the receiver circuit 13.

Referring to FIG. 5, demagnetizing field generated upon reception of the electric energy by the receiver antenna 12 will be described.

The demagnetizing field refers to the magnetic field generated inside the magnetic body. Referring to FIG. 5, the magnetic flux M generated by the transmission antenna 5 and collected by the core 12a passes the inside the core 12a. Then the core 12a through which the magnetic flux M passes performs the magnetic polarization in the longitudinal direction, and generates the magnetic field in the direction opposite the one in which the magnetic flux Ma passes the inside, that is, the demagnetizing field. The demagnetizing field generates the magnetic flux Mb in the direction opposite the magnetic flux Ma. The effective magnetic flux Ma interlinked with the receiver coil 12b is reduced under the influence of the magnetic flux Mb generated due to the demagnetizing field compared with the magnetic flux M collected by the core 12a.

The demagnetizing field is enlarged as the magnetic polarization becomes large and the inter-pole distance becomes short. In other words, the demagnetizing field is enlarged as the diameter of the core 12a becomes large and the length of the core 12a becomes short, indicating its dependence on the aspect ratio (length/diameter of core 12a).

The correlation between the change in the aspect ratio which depends on the length and diameter of the core 12a of the receiver antenna 12 and the fluctuation of the received electric power will be described.

Referring to FIG. 6, the fluctuation in the received electric power caused by the change in the aspect ratio (L/d) derived from changing the length L of the core 12a along the longitudinal axis while keeping the diameter d of the core 12a of the receiver antenna 12 constant is shown in Table of FIG. 7, and the results are shown in the graph of FIG. 8.

In FIGS. 7 and 8, each received electric power at the respective aspect ratios is defined as 1 when the aspect ratio of the core 12a is set to 1. Referring to the table in FIG. 7, the verification is performed with respect to the change in the received electric power obtained when the receiver antenna 12 formed by winding the receiver coil 12b evenly around the ferrite core (manufactured by company A) by 50 times is disposed in the even magnetic field while setting the diameter d of the core 12a to 1 mm and changing the length L thereof. The uniform direction of the magnetic field is in accordance with directions of the winding axis of the receiver coil 12b and the longitudinal axis of the core 12a. That is, they are in parallel with one another (the angle defined thereamong is 0°).

The verification results shown in FIGS. 7 and 8 indicate that the received electric power is sharply increased at a time point when the aspect ratio becomes 10 or more. When the aspect ratio is set to 10 or more to suppress the demagnetizing field inside the core 12a, the magnetic flux Mb generated due to the demagnetizing field is reduced. Accordingly, the effective magnetic flux Ma is increased to intensify the received electric power.

In other words, when the aspect ratio is set to 10 or more, the demagnetizing field is considerably reduced to make the level of the received power 247 times higher than the case where the aspect ratio is set to 1 When the aspect ratio is set to 10, the normalized received electric power becomes theoretically half or 123.5 ($247/2$) times higher even if the angle defined by the direction of the magnetic flux M generated by the transmission antenna 5 and the winding axis of the receiver coil becomes 45°, resulting in sufficiently high electric power.

The receiver antenna 12 in the case where the aspect ratio is set to 10 is capable of receiving higher electric power compared with the receiver antenna with the core 12a in the case where the aspect ratio is set to 5 when the angle defined by the direction of the magnetic flux M generated by the transmission antenna 5 is in accordance with the winding axis of the receiver coil 12b and the longitudinal axis of the core 12a (0°).

Even if each angle defined by the direction of the magnetic flux M generated by the power feeding antenna 5, the winding axis of the receiver coil 12b, and the longitudinal axis of the core 12a having the aspect ratio set to 10 or more is increased, the electric power required for driving the capsulated endoscope 3 may be supplied. The verification was performed while keeping the applied magnetic field and frequency constant. However, the verification indicates that the normalized received electric power is kept unchanged even if the size of the uniform magnetic field or the frequency is changed so long as the core 12a is not magnetically saturated.

As described above, in the embodiment, the aspect ratio is increased to 10 or more by forming the core 12a of the receiver antenna 12 to be thin and long such that the influence of the demagnetizing field is suppressed. This makes it possible to increase the effective magnetic fluxes Ma interlinked with the receiver coil 12b.

This makes it possible to improve the power receiving efficiency of the receiver antenna 12, and feed the electric power in the stable state. The increase in the power receiving efficiency allows the capsulated endoscope 3 to be driven even if angles defined by the direction of the magnetic flux M generated by the transmission antenna 5, the longitudinal axis of the core 12a having the aspect ratio set to 10 or more, and the winding axis of the receiver coil 12b become large compared with the generally employed receiver antenna.

The process for winding the receiver coil will be described. It has been clarified that the influence of the demagnetizing field to the center of the core 12a is smaller than the influence to the end of the core 12a. Accordingly, in the case where the winding number is the same, the winding the receiver coil 12b around the core 12a tightly at the center which is less influenced under the demagnetizing field makes the power receiving efficiency higher than the case for winding the coil around the core 12a over the entire surface uniformly as shown in FIG. 9.

If the electric power required for electrically driving the capsulated endoscope function portion 14 cannot be received by the receiver antenna 12, the capsulated endoscope 3 according to the embodiment is structured to allow the emergency battery 20 to feed the auxiliary power. The aforementioned case refers to the state where the angles formed among the direction of the magnetic flux M generated by the transmission antenna 5, the longitudinal axis of the core 12a having the aspect ratio set to 10 or more, and the winding axis of the receiver coil 12b are 90°.

Second Embodiment

Figure 10:
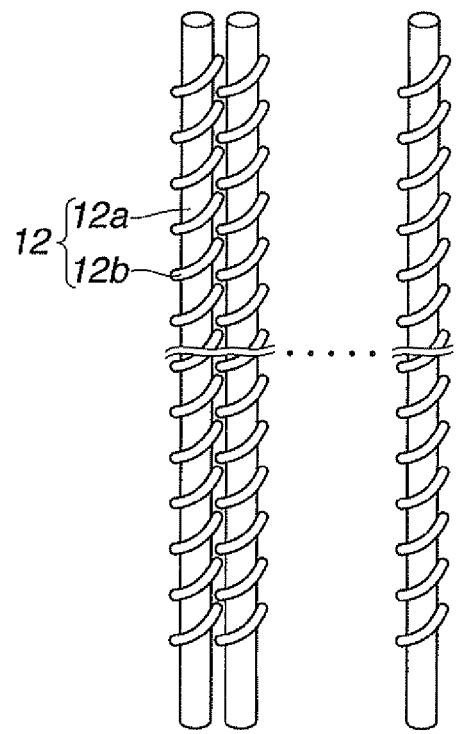
FIG. 10 is a view showing a plurality of receiver antennas in a single wireless power supply system according to a second embodiment.
Figure 11:
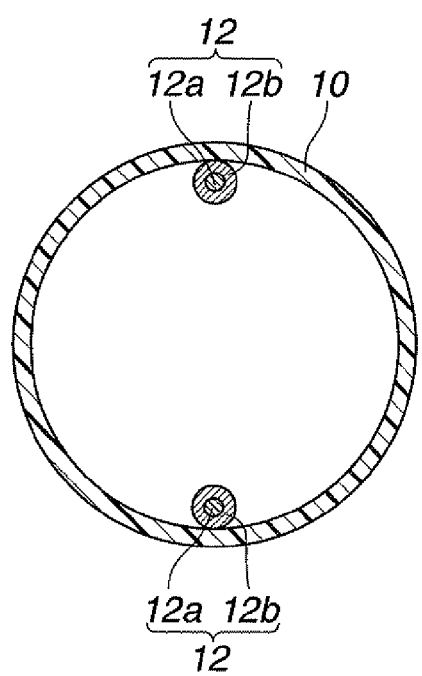
FIG. 11 is a transverse sectional view of a capsulated endoscope as a first modified example.
Figure 12:
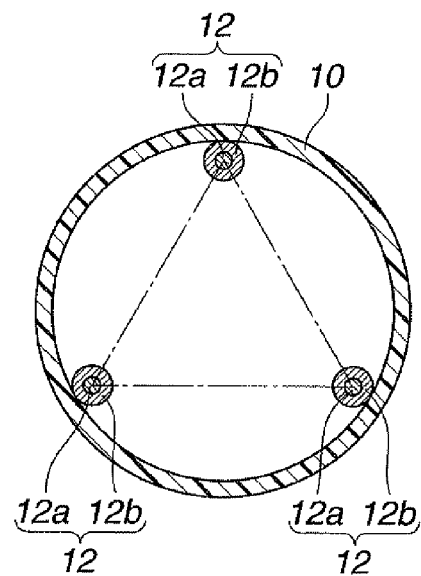
FIG. 12 is a transverse sectional view of a capsulated endoscope as a second modified example.
Figure 13:
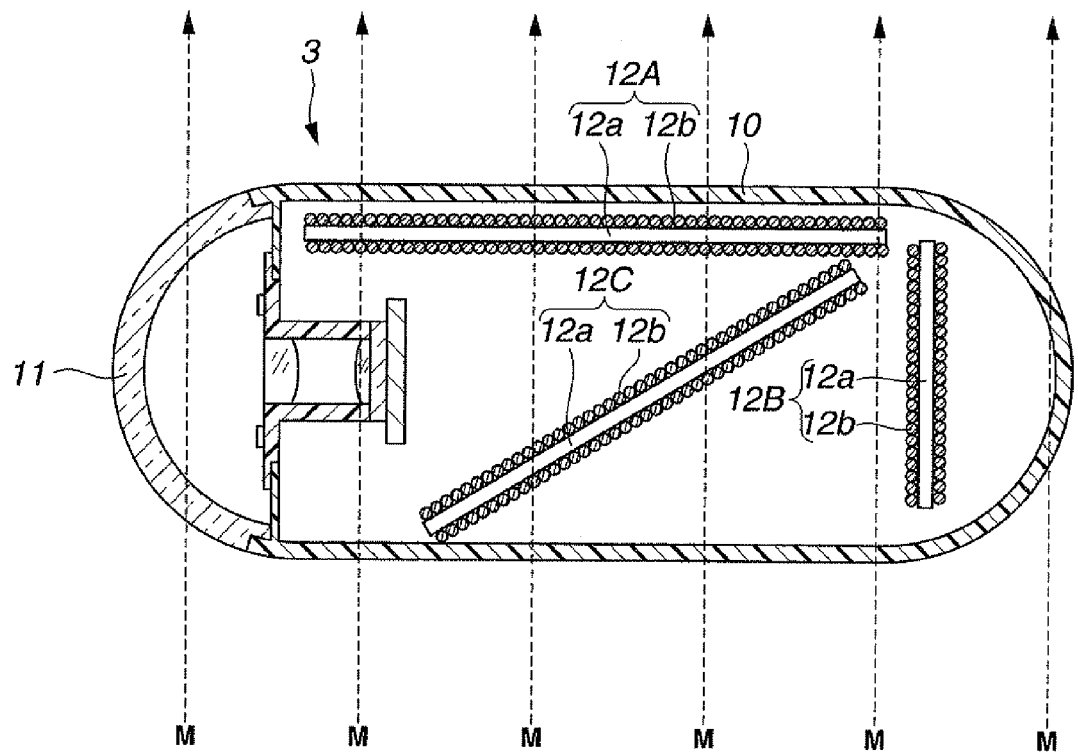
FIG. 13 is a longitudinal sectional view of a capsulated endoscope as a third modified example.

A second embodiment according to the present invention will be described referring to FIGS. 10 to 13. FIG. 10 is a view showing a plurality of receiver antennas in a single wireless power supply system. FIG. 11 is a transverse sectional view of a capsulated endoscope as a first modified example. FIG. 12 is a transverse sectional view of a capsulated endoscope as a second modified example. FIG. 13 is a longitudinal sectional view of a capsulated endoscope as a third modified example.

In the following explanation, the same components as those of the capsulated endoscopic system 1 of the first embodiment will be designated with the same reference numerals, and explanations thereof, thus will be omitted. The other components of the capsulated endoscope including the known light source, the image pickup optical system, the image pickup device, and the electronically controlled unit are not shown for simplifying the drawing.

The basic structure of the embodiment is substantially the same as that of the first embodiment except that plural receiver antennas 12 are connected in series or in parallel as shown in FIG. 10. The winding number and winding process of the receiver coil are the same as those shown in FIG. 5.

Likewise the first embodiment, in the embodiment, the magnetic flux M generated by the transmission antenna 5 interlinks with the receiver coil 12b. As the plural receiver antennas 12 are disposed in the embodiment, the number of the interlinked magnetic flux M may be increased compared with the case where only the single receiver antenna 12 is employed. In the generally employed system, the diameter of the capsulated endoscope 3 is required to be enlarged for improving the power receiving efficiency. In the embodiment, the plural receiver antennas 12 are disposed to further improve the power receiving efficiency of the receiver antenna 12 without increasing the diameter of the capsulated endoscope 3 compared with the first embodiment. The capsulated endoscope 3 may be driven in the more stable state.

In the embodiment, the respective receiver antennas 12 are disposed adjacent with one another as shown in FIG. 10. However, those receiver antennas 12 may be disposed at predetermined intervals.

As a first modified example of FIG. 11 shows, two receiver antennas 12 are disposed in the capsulated endoscope 3 such that they are apart from each other by the farthest distance. Likewise, a second modified example of FIG. 12 shows that three receiver antennas 12 are arranged at the respective peaks of the equilateral triangle.

In the first and the second modified examples, the mutual inductance of the plural receiver antennas 12 may be minimized compared with the case where the receiver antennas 12 are disposed adjacent with one another. The power receiving efficiency of the receiver antenna 12 is expected to be further improved.

In the second modified example, three receiver antennas 12 are employed. However, the number of the receiver antennas is not limited to three, but may be set to the arbitrary number so long as it is the plural number. If the plural antennas are disposed at the respective peaks of the regular polygon, the mutual inductance of the respective receiver antennas 12 may be minimized. Accordingly, further improvement in the power receiving efficiency is expected.

In the first and the second modified examples, each longitudinal axis of the respective receiver antennas 12 is directed in the same direction, that is, in parallel with one another. In the third modified example shown in FIG. 13, three receiver antennas are disposed such that each longitudinal axis of the cores 12a, and each winding axis of the receiver coils 12b are directed in the different directions.

In the aforementioned case, even if the angle defined by the longitudinal axis of one of the receiver antennas 12 and the magnetic flux M generated by the transmission antenna 5 becomes 90°, failing to receive the electric power, the angle defined by the longitudinal axis of the other receiver antenna 12 and the magnetic flux M generated by the transmission antenna 5 does not become 90°. Accordingly, the electric power may be received in the stable state irrespective of the orientation of the capsulated endoscope 3 in the body cavity of the subject 100.

Referring to FIG. 13, when the magnetic flux M moves toward the arrow direction, the electric power cannot be received by one of those three receiver antennas 12, that is, a receiver antenna 12A as the angle formed with the magnetic flux become 90°. However, the other receiver antenna 12B has the longitudinal axis in accord with that of the magnetic flux M (in parallel), and the other receiver antenna 12C which is thin and long allows the aspect ratio to be set to a large value. Accordingly, sufficient electric power may be received even if the angle defined by the magnetic flux M and the longitudinal axis becomes large. This allows the sufficient electric power to be received for driving the capsulated endoscope 3 to be received.

In the explanation, the number of the receiver antennas 12 to be employed is set to three. However, the arbitrary number may be set so long as it is the plural number. Each aspect ratio of the core 12a of the respective receiver antennas 12, and the winding number and the winding mode of the receiver coil 12b may be independently set. The plural receiver antennas 12 to be employed may be disposed such that at least one receiver antenna is oriented in the different direction from the other receiver antennas.

In the first and the second embodiment as well as the modified examples thereof, the wireless power supply system is applied to the capsulated endoscopic system 1. However, it is to be understood that the wireless power supply system according to the present invention may be widely applied to the device for transmitting and receiving the electric power through the wireless power feeding mode.

The present invention realizes the structure for efficiently receiving the electric energy wirelessly transmitted from the wireless power supply system, and provides the wireless power supply system which contributes to the improved power receiving efficiency, the capsulated endoscope which applies the system, and the capsulated endoscopic system.

It is to be understood that the present invention formed as the respective embodiments may be modified into various forms at the stage of implementing the invention without departing from the scope of the invention. As the aforementioned embodiments contain the invention at various stages, various inventions may be extracted through the arbitrary combination of the disclosed plural elements.

For example, if the problem may be solved by the invention to provide the effect as described above even when a certain number of the elements are eliminated from all the elements introduced in the respective embodiments, the structure having the elements eliminated may be extracted as the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsulated endoscope comprising:
   a receiver antenna formed by winding a receiver coil around an outer periphery of a substantially bar-like core member for wirelessly receiving an electric power, the core member being solid and formed of a high magnetic permeability magnetic material,
   wherein the core member of the receiver antenna is arranged in a longitudinal direction along an outer case of the capsulated endoscope,
   wherein a length of the core member of the receiver antenna is 10 to 15 times longer than a diameter of the core member, and the receiver coil of the receiver antenna is tightly wound around a center of the core member, wherein a plurality of the receiver antennas are disposed in which the receiver coils are electrically connected in series or in parallel, and wherein the plurality of the receiver antennas have longitudinal axes of the core members arranged in parallel, and are disposed at respective peaks of a regular polygon, with respect to the outer case.

2. A capsulated endoscopic system comprising:

a power feeding system equipped with a transmission antenna for wirelessly transmitting an electric power from a power source; and a capsulated endoscope which contains a receiver antenna formed by winding a receiver coil around an outer periphery of a substantially bar-like core member for receiving the transmitted electric power, wherein the core member of the receiver antenna is arranged in a longitudinal direction along an outer case of the capsulated endoscope, wherein a length of the core member of the receiver antenna is 10 to 15 times longer than a diameter of the core member, and the receiver coil of the receiver antenna is tightly wound around a center of the core member, wherein a plurality of the receiver antennas have the receiver coils electrically connected in series or in parallel, and wherein the plurality of the receiver antennas have longitudinal axes of the core members arranged in parallel, and are disposed at respective peaks of a regular polygon, with respect to the outer case.

* * * * *